(12) United States Patent
Ohki et al.

(10) Patent No.: US 6,408,846 B1
(45) Date of Patent: Jun. 25, 2002

(54) INHALATION TYPE DRUG DISPENSER

(75) Inventors: Hisatomo Ohki; Kazunori Ishizeki; Shigemi Nakamura; Yoshiyuki Yazawa, all of Gunma; Akira Yanagawa, Yokohama, all of (JP)

(73) Assignees: Unisia Jecs Corporation, Atsugi; Dott Limited Company, Yokohama, both of (JP)

( * ) Notice: Subject to any disclaimer, the term of this patent is extended or adjusted under 35 U.S.C. 154(b) by 0 days.

(21) Appl. No.: 09/623,457
(22) PCT Filed: Dec. 27, 1999
(86) PCT No.: PCT/JP99/07304
§ 371 (c)(1),
(2), (4) Date: Sep. 11, 2000
(87) PCT Pub. No.: WO00/41756
PCT Pub. Date: Jul. 20, 2000

(30) Foreign Application Priority Data

Jan. 11, 1999 (JP) ............................................. 11-004671

(51) Int. Cl.⁷ ............................................. A61M 15/00
(52) U.S. Cl. .............................. 128/203.15; 128/203.21
(58) Field of Search ....................... 128/200.24, 203.15, 128/203.21, 203.12, 203.23; 604/58–60

(56) References Cited

U.S. PATENT DOCUMENTS 6,234,169 B1 * 5/2001 Bulbrook et al. ...... 128/203.15
6,273,086 B1 * 8/2001 Ohki et al. ............ 128/203.15
6,341,605 B1 * 1/2002 Ohki et al. ............ 128/203.15

FOREIGN PATENT DOCUMENTS

| JP | 7-313599 | 12/1995 |
| JP | 9-248342 | 9/1997 |
| JP | 10-216204 | 8/1998 |

* cited by examiner

Primary Examiner—Glenn K. Dawson
(74) Attorney, Agent, or Firm—Foley & Lardner

(57) ABSTRACT

A diffusion chamber block 14 is provided in a block mounting hole 13A of an inhalant port 13, and a granular medicine diffusion chamber 17 is formed in the diffusion chamber block 14. The granular medicine diffusion chamber 17 is formed at a side of the inhalant port 13 with a granular medicine inflow opening 17A and at a side of a capsule housing hole 9 with a granular medicine outflow opening 17B. A diffusion chamber in flow passage 18 is provided to communicate an outflow air passageway 12 with the granular medicine inflow opening 17A, whereas a diffusion chamber outflow passage is provided to communicate the granular medicine outflow opening 17B with the inhalant port 13. When inhaling granular medicines in the capsule housing hole 9 via the inhalant port 13 by way of breathing action, there results in counter-flow vortex within the granular medicine diffusion chamber 17. The counter-flow cortex acts to finely break and atomize massive granular medicines, thus promoting atomization of the granular medicines.

7 Claims, 8 Drawing Sheets

INHALATION TYPE DRUG DISPENSER

TECHNICAL FIELD

Figure 1:
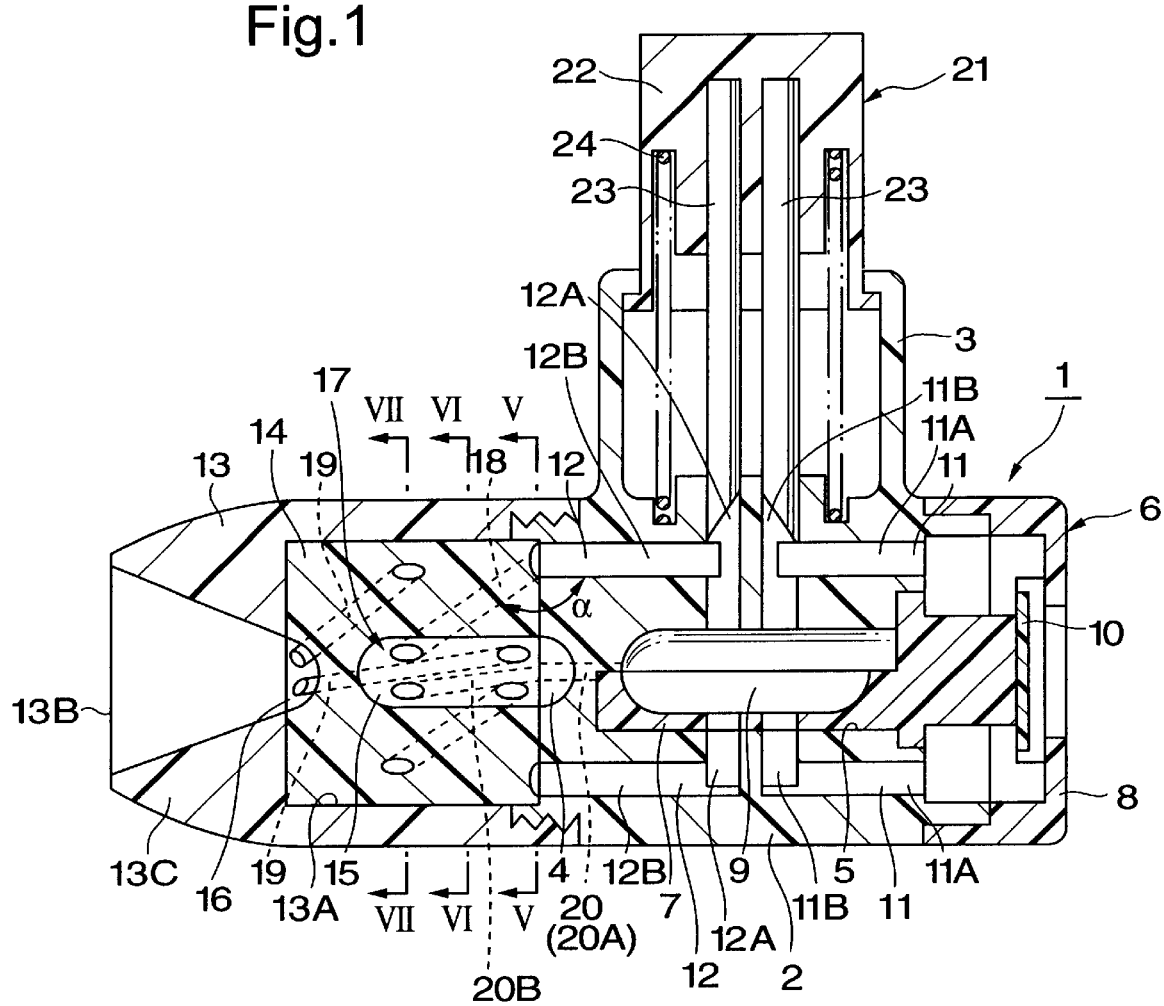
Figure 2:
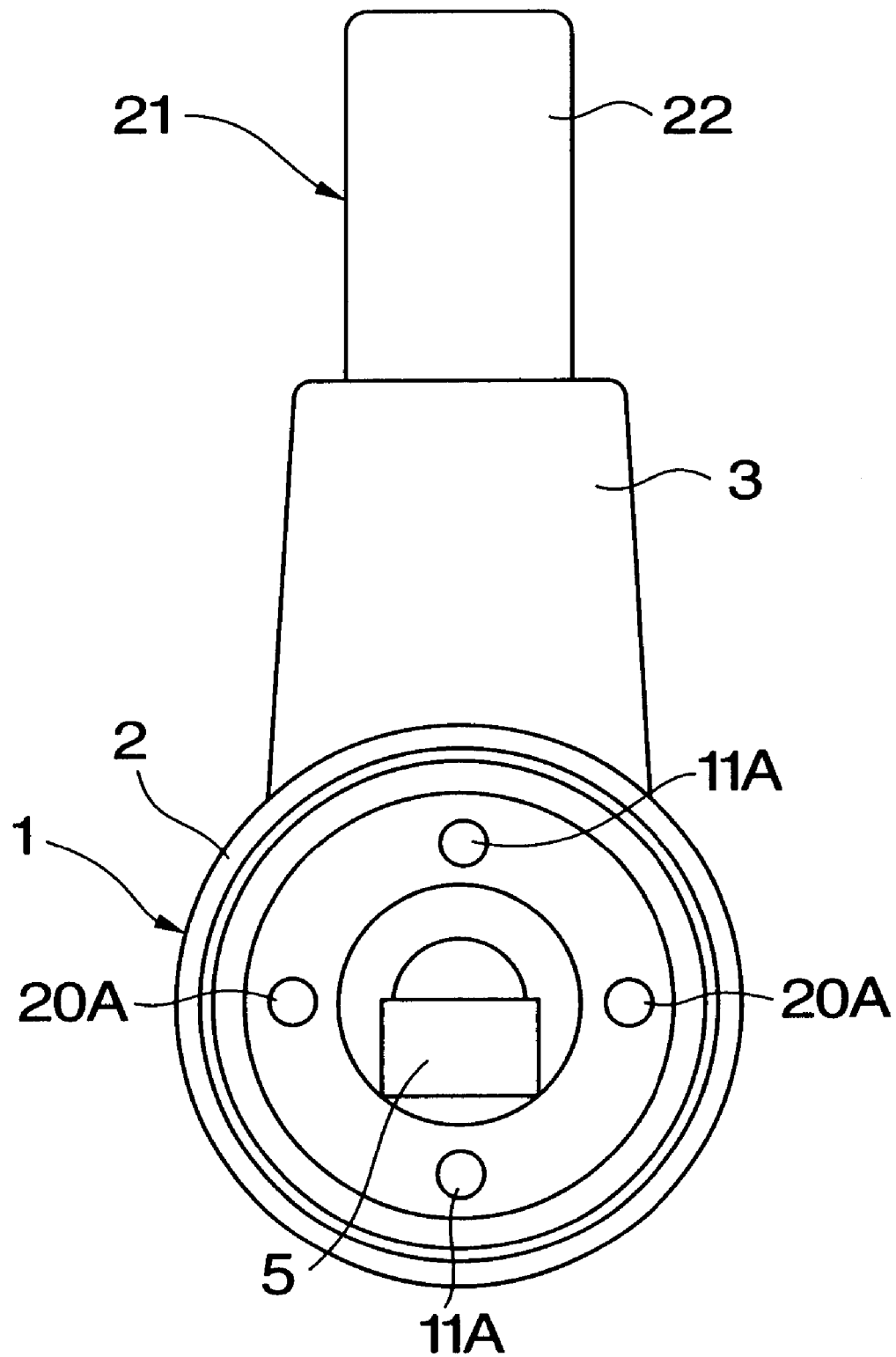
Figure 3:
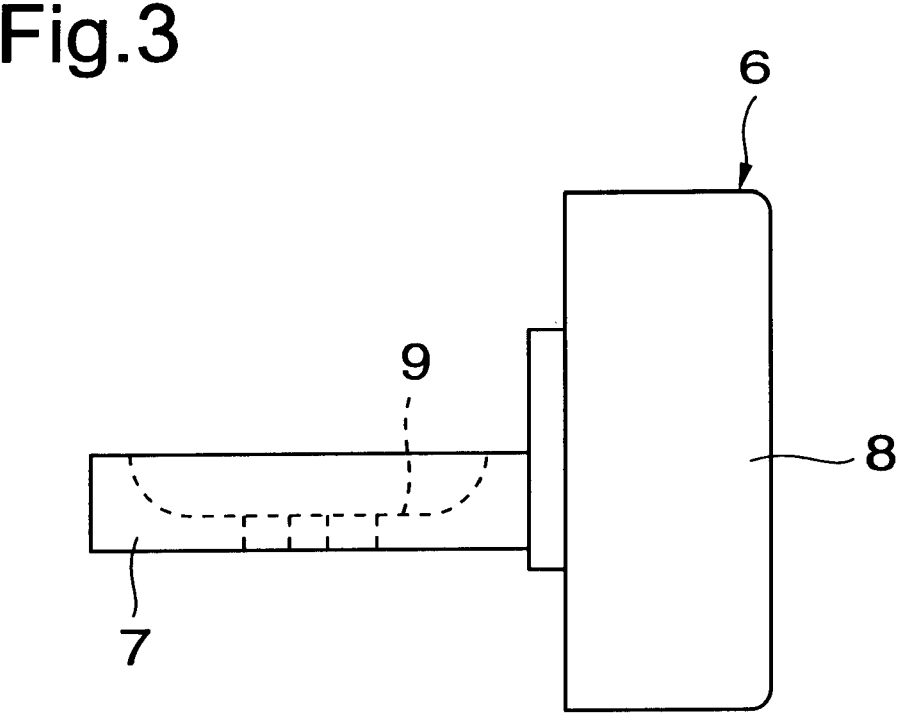
Figure 4:
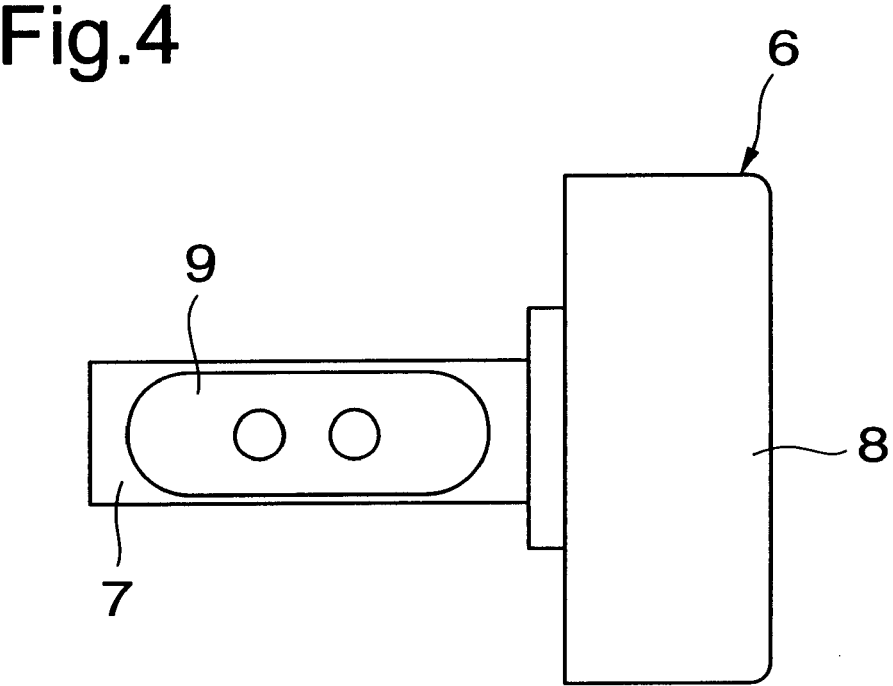

The invention relates to an inhalant medicator suitable to prescribe granular medicines toward within lungs of a patient by way of breathing action of the patient.

BACKGROUND ART

Generally, there are various medications of prescribing granular medicines toward within lungs of an asthmatic patient. Of these, an inhalant medicator used for an inhalation treatment where encapsulated granular medicines are inhaled, has been disclosed in Japanese Patent Provisional Publication Nos. 7-313599 and 10-216204.

The inhalant medicator as disclosed in the above Japanese Patent Provisional Publications is generally comprised of a medicator body equipped at one axial end with a granular medicine accommodation chamber and at the other axial end with an inhalant port used for inhalation of granular medicines, and air passageways provided to supply granular medicines in the granular medicine accommodation chamber of the medicator body toward a side of the inhalant port, and also constructed in such a manner as to charge granular medicines in the granular medicine accommodation chamber by means of a capsule or the like.

In such inhalant medicators, when prescribing granular medicines via the inhalant port into the lungs of a patient, a capsule is, first, installed in a granular medicine accommodation chamber. Then, through holes are pricked in the capsule by means of a boring tool. Under this condition, when the patient draws his or her breath while taking the inhalant port in his or her mouse, air flow occurs owing to air sucked in the atmosphere side and flowing through the air passageways, and then the air flow carries the granular medicines in the granular medicine accommodation chamber within toward the inhalant port. In this manner, the granular medicines, flowing out of the capsule, could be inhaled into the lungs of the patient.

As discussed above, in the conventional inhalant medicators, granular medicines stored in a granular medicine accommodation chamber, are diffused or agitated by way of fluid flow of air flowing via the air passageways into the granular medicine accommodation chamber. However, during medication with a granular medicine having a strong condensation property (bad dispersion), or a powdered medicine having a greatly increased tendency to be charged with static electricity, or the like, there is a problem of unstable dispersion of the granular or powdered medicine, that is, a possibility of flowing out a lump of granular or powdered medicines within toward the inhalant port. As a result, there is a possibility that a lump of granular or powdered medicines tend to be dropped in the oral cavity or the mouse of the patient without sufficient dispersion during the inhalation, thus preventing medical prescription of a specified amount of granular or powdered medicines into the patient's lungs. This lowers medical benefits of the granular or powdered medicines.

It is, therefore, in view of the previously-described disadvantages of the prior art, an object of the present invention to provide an inhalant medicator which is capable of prescribing a specified amount of granular or powdered medicines stored in a medicator body toward within lungs of a patient by widely dispersing and micronizing the granular or powdered medicines having a bad dispersion property.

DISCLOSURE OF THE INVENTION

In order to accomplish the aforementioned and other objects, according to the invention as claimed in claim 1, an inhalant medicator comprises a medicator body formed at one axial end with a granular medicine accommodation chamber and at the other axial end with an inhalant port for inhalation of granular medicines, an inflow air passageway communicating an atmosphere side with the granular medicine accommodation chamber for supplying air into the granular medicine accommodation chamber of the medicator body, an outflow air passageway through which the granular medicines of the granular medicine accommodation chamber are flown out, and a granular medicine diffusion chamber disposed between the inhalant port and the granular medicine accommodation chamber and formed with an inflow opening located at a side of the inhalant port and an outflow opening located at a side of the granular medicine accommodation chamber, a diffusion chamber inflow passage communicating the outflow air passageway with the inflow opening of the granular medicine diffusion chamber, and a diffusion chamber outflow passage communicating the outflow opening of the granular medicine diffusion chamber with the inhalant port.

In the inhalant medicator made according to the invention defined in claim 1, when a patient draws his or her breath via the inhalant port, air flows via the inflow air passageway into the granular medicine accommodation chamber, and thus the granular medicines in the granular medicine accommodation chamber can be carried into the granular medicine accommodation chamber through the outflow air passageway. At this time, the outflow air passageway is communicated with the inflow opening of the granular medicine diffusion chamber located at the side of the inhalant port, while the outflow opening of the granular medicine diffusion chamber located at the side of the granular medicine accommodation chamber is communicated with the inhalant port. With the previously-noted arrangement, there occurs counter-flow vortex flowing from the other axial end to the one axial end of the medicator body within the granular medicine diffusion chamber. Therefore, the granular medicines fed via the diffusion chamber inflow passage into the granular medicine diffusion chamber, are blended by way of the counter-flow vortex. As a result of this, even in case of a lump of granular medicines having a bad dispersion property, it is possible to finely break or smash and micronize the granular medicines.

According to the invention as claimed in claim 2, a bending angle of a connecting portion connecting the outflow air passageway and the diffusion chamber inflow passage, is configured to form an obtuse angle. Therefore, it is possible to prevent the granular medicines fed through the diffusion chamber inflow passage and the diffusion chamber outflow passage from being accumulated in the connecting portion, thus effectively carrying the granular medicines.

In the inhalant medicator made according to the invention defined in claim 3 or 4, the diffusion chamber outflow passage is formed with a bent portion so that the bent portion strides over the diffusion chamber inflow passage. Therefore, it is possible to prevent the granular medicines flowing out of the granular medicine diffusion chamber from being accumulated in the bent portion, thus effectively carrying the granular medicines.

In the inhalant medicator made according to the invention defined in claim 5, 6 or 7, the diffusion chamber inflow passage is provided to open to an eccentric position with respect to a longitudinal axis of the granular medicine diffusion chamber so that the diffusion chamber inflow passage extends in a direction tangent to the granular medicine diffusion chamber as seen from a lateral cross-sectional view of the granular medicine diffusion chamber. Thus, it is possible to give a whirling flow action to air flowing from the outflow air passageway into the granular medicine diffusion chamber, thereby ensuring turbulent air flow created by adding the whirling air flow to counter-flow vortex within the granular medicine diffusion chamber. As a consequence, by virtue of the turbulent air flow, it is possible to promote micronization or atomization of the granular medicines.

BRIEF DESCRIPTION OF THE DRAWINGS

FIG. 1 is a longitudinal cross-sectional view illustrating an embodiment of an inhalant medicator.

FIG. 2 is a right-hand side view of the inhalant medicator shown in FIG. 1, under a condition that a capsule holder is removed from a medicator body.

FIG. 3 is an elevation view of the capsule holder shown in FIG. 1.

FIG. 4 is a plan view of the capsule holder shown in FIG. 3.

FIG. 5 is a lateral cross section as viewed from the direction of the arrow V—V of FIG. 1.

FIG. 6 is a lateral cross section as viewed from the direction of the arrow VI—VI of FIG. 1.

FIG. 7 is a lateral cross section as viewed from the direction of the arrow VII—VII of FIG. 1.

FIG. 8 is a schematic perspective view of a diffusion chamber block formed therein with a granular medicine diffusion chamber, a diffusion chamber inflow passage, and a diffusion chamber outflow passage.

FIG. 9 is a schematic perspective view showing fluid flow of air flowing through the diffusion chamber inflow passage and the diffusion chamber outflow passage of the granular medicine diffusion chamber.

FIG. 10 is a longitudinal cross section of the inhalant medicator, as viewed from the same position as FIG. 1, under a particular condition where the capsule is removed by pulling out the capsule holder.

FIG. 11 is a schematic longitudinal cross section of the inhalant medicator under a particular condition where granular medicines encapsulated in the capsule are inhaled.

DESCRIPTION OF THE PREFERRED EMBODIMENTS

The present invention will be hereinbelow described in detail in reference to the drawings (FIGS. 1 through 11) attached hereto.

Referring now to FIGS. 1 through 11, reference sign 1 denotes a medicator body constructing an essential part of the inhalant medicator. The medicator body 1 is comprised of a body 2 described later, a capsule holder 6, an inhalant port 13, and a diffusion chamber block 14.

A portion denoted by reference sign 2 is the body provided in such a manner as to locate at one side of the medicator body 1. The body 2 is formed into a substantially cylindrical shape, and also formed on its outer periphery with a boring tool guide 3 which movably supports a support portion 22 of a boring tool 21 described later. The body is also formed on the other side wall with a diffusion chamber side recessed portion 4 constructing part of a granular medicine diffusion chamber 17 described later. Also formed in the body 3 are a holder accommodation portion 5, an inflow air passageway 11, and an outflow air passageway 12. An inhalant port 13 and a diffusion chamber block 14 are also provided on the body.

A portion denoted by reference sign 5 is the holder accommodation portion provided on the inner periphery of the body 2 and retractably and extendably accommodating a capsule holding portion 7 of the capsule holder 6. As shown in FIG. 2, the holder accommodation portion 5 is located close to the lower side of the body 2, and formed as a substantially rectangular through opening extending in the axial direction of the body 2.

A portion denoted by reference sign 6 is the capsule holder detachably mounted on the body 2. As shown in FIG. 3, the capsule holder 6 is mainly constructed by the capsule holding portion 7 retractably and extendably fitted into the holder accommodation portion 5 of the body 2, and a cap 8 used to catch the capsule holding portion 7 when putting in and out the capsule holding portion. Under a condition that the capsule holding portion 7 is inserted into the holder accommodation portion 5, the capsule holder 6 is capable of forming a capsule housing hole 9 (serving as a granular medicine accommodation chamber) between the capsule holding portion 7 and the holder accommodation portion 5. Additionally, a check valve 10 is built in the cap 8 so as to prevent back flow of granular medicines owing to coughing during medication.

Portions denoted by reference signs 11, 11 are inflow air passageways provided at one side of the body 2. Each of the inflow air passageways 11 is constructed by an inflow passage 11A located on the outer periphery of the capsule housing hole 9 and extending in the axial direction, and a pin insertion hole 11B communicating with the inflow passages 11A and penetrating the capsule housing hole 9 in the radial direction. These inflow air passageways 11 are provided to flow outside air toward within the capsule housing hole 9. Pins 23, 23 of the boring tool 21 are inserted into the respective pin insertion holes 11B, 11B.

Portions denoted by reference signs 12, 12 are outflow air passageways provided at the other side of the body 2. Each of the outflow air passageways 12 is constructed by a pin insertion hole 12A penetrating the capsule housing hole 9 in the radial direction, and an outflow passage 12B communicating with the pin insertion hole 12A and extending in the axial direction. Each of the outflow air passageways 12 is provided to supply the granular medicines in the capsule housing hole 9 toward within the inhalant port 13 described later. Pins 23, 23 of the boring tool 21 are inserted into the respective pin insertion holes 12A, 12A.

A portion denoted by reference sign 13 is the inhalant port detachably installed on the other side of the body 2. The inhalant port 13 is formed into a substantially cylindrical shape. The inhalant port is threadably received at one end onto the body 2. Also, the outer periphery of the free end (the other end) of the inhalant port is gradually diametrically diminished toward the outer side for the purpose of easily holding the inhalant port in his or her mouse of the patient. Also, the inhalant port 13 is formed at its base end with a block mounting hole 13A bored therein so that the diffusion chamber block 14 (described later) is accommodated in the diffusion chamber block. The inhalant port is also formed at its tip end with a diametrically enlarged portion 13C serving as a discharge outlet 13B.

A portion denoted by reference sign 14 is the diffusion chamber block provided in the block mounting hole 13A. The diffusion chamber block 14 is formed into a cylindrical shape in such a manner as to be inserted into the block mounting hole 13A located on the axial line of the inhalant port of the inhalant medicator 1. The diffusion chamber block 14 is formed with an elongated hole 15 centrally axially extending from one end to the other end. The diffusion chamber block is formed at the center of its other face opposing to the elongated hole with a discharge side recessed portion 16 communicating the inner peripheral wall surface of the inhalant port 13.

A portion denoted by reference sign 17 is a granular medicine diffusion chamber arranged in the axial direction of the diffusion chamber block 14. The granular medicine diffusion chamber 17 is constructed by the diffusion chamber side recessed portion 4 formed in the body 2, and the elongated hole 15 formed in the diffusion chamber block 14. The granular medicine diffusion chamber 17 is arranged between the capsule housing hole 9 and the inhalant port 13. Also, the granular medicine diffusion chamber 17 is formed therein with two granular medicine inflow openings 17A at a side of the inhalant port 13, in a manner such that the two granular medicine inflow openings are circumferentially spaced apart from each other substantially 180 degrees. The granular medicine diffusion chamber is formed therein with four granular medicine outflow openings 17B at a side of the capsule housing hole 9, in a manner such that the four granular medicine outflow openings are circumferentially spaced apart from each other substantially 90 degrees. Additionally, the granular medicine diffusion chamber is formed therein with two auxiliary air inflow openings 17C at the side of the inhalant port 13, in a manner such that the two auxiliary air inflow openings are circumferentially offset from the respective granular medicine inflow openings 17A by substantially 90 degrees. The granular medicine diffusion chamber 17 is provided to finely break the granular medicines fed together with air flowing through each of the diffusion chamber inflow passages 18 described later.

Portions denoted by reference signs 18, 18 are the diffusion chamber inflow passages. As shown in FIGS. 5 through 9, each of the diffusion chamber inflow passages 18 is bored at a position spaced apart from the diffusion chamber block 14 by 180 degrees in the circumferential direction in such a manner as to communicate the outflow passage 12B of the outflow air passageway 12 with the granular medicine inflow opening 17A of the granular medicine diffusion chamber 17. As can be seen from FIG. 1, the angle α of the connecting portion, which connects the diffusion chamber inflow passage 18 and the outflow passage 12B, is an obtuse angle. Furthermore, the diffusion chamber inflow passage 18 is formed to open to the eccentric position with respect to the longitudinal axis of the granular medicine diffusion chamber 17 so that the diffusion chamber inflow passage 18 extends in a direction tangent to the granular medicine diffusion chamber 17 as seen from the lateral cross-sectional view of the granular medicine diffusion chamber 17.

Figure 11:
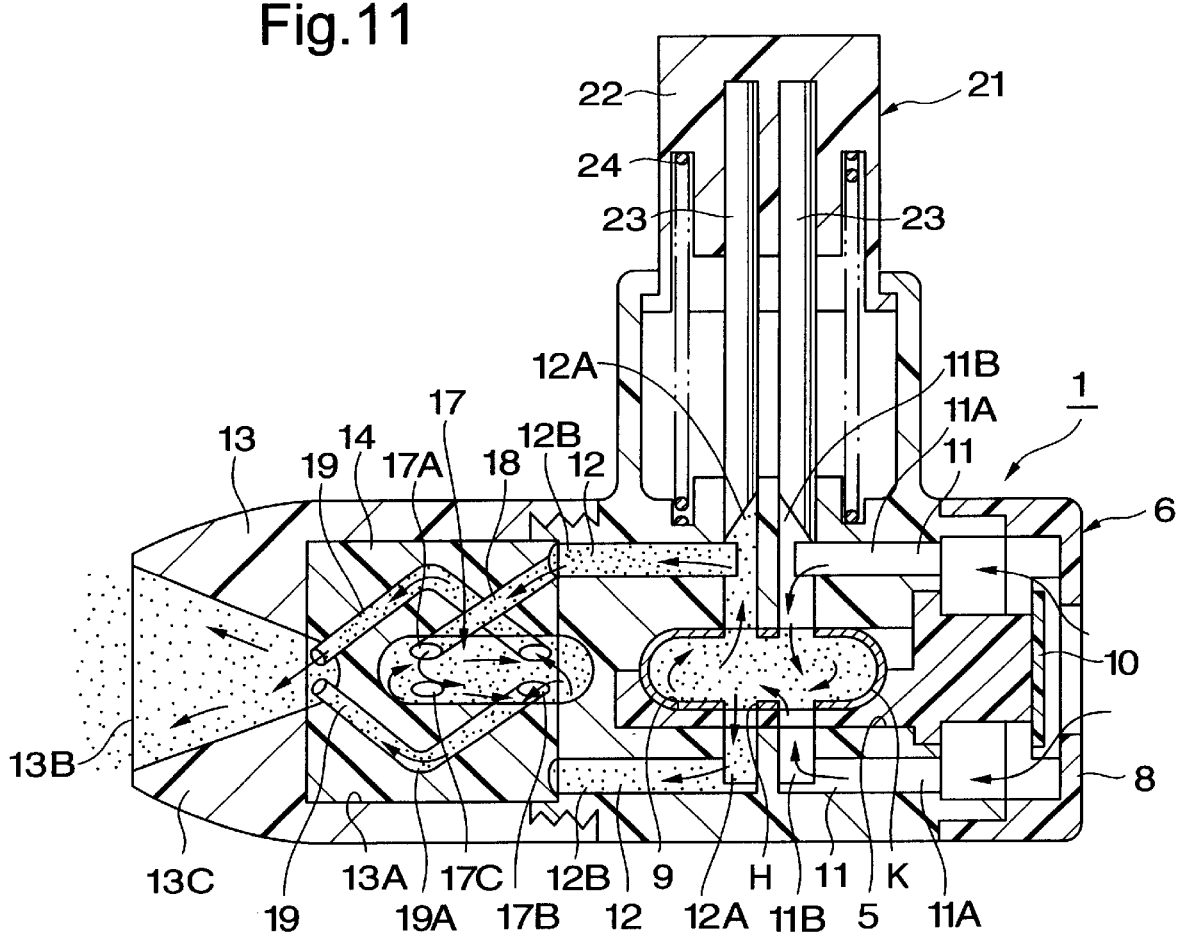

Portions denoted by reference signs 19, 19 . . . are four diffusion chamber outflow passages formed in the diffusion chamber block 14 in a manner so as to be circumferentially spaced apart from each other substantially 90 degrees. As shown in FIGS. 5 through 9, each of the diffusion chamber outflow passages 19 serves to communicate the granular medicine outflow opening 17B of the granular medicine diffusion chamber 17 with the inhalant port 13. The respective diffusion chamber outflow passage is formed and bent into a substantially L shape in such a manner as to stride over the associated diffusion chamber inflow passage 18. As shown in FIG. 8, the bending angle $\beta$ of the bent portion 19A of the diffusion chamber outflow passage is an obtuse angle. Also, each of the diffusion chamber outflow passages 19 opens to the eccentric position with respect to the longitudinal axis of the granular medicine diffusion chamber 17 so that each of the diffusion chamber outflow passages 19 extends in a direction tangent to the granular medicine diffusion chamber 17 as seen from the lateral cross-sectional view of the granular medicine diffusion chamber 17. Each of the diffusion chamber outflow passages 19 is provided to discharge air in the granular medicine diffusion chamber 17 via the discharge side recessed portion 16 toward within the inhalant port 13.

Portions denoted by reference signs 20, 20 are the auxiliary air passages formed in both the body 2 and the diffusion chamber block 14. Each of the auxiliary air passages 20 is constructed by a first auxiliary passage 20A formed at a position circumferentially offset from the outflow air passageway 12 by 90 degrees in such a manner as to penetrate the body 2 in the axial direction, and a second auxiliary passage 20B bored in the diffusion chamber block 14 and communicating with the auxiliary air inflow opening 17C of the granular medicine diffusion chamber 17. Also, the second auxiliary passage 20B opens to the eccentric position with respect to the longitudinal axis of the granular medicine diffusion chamber 17 so that the second auxiliary passage 20B extends in a direction tangent to the granular medicine diffusion chamber 17 as seen from the lateral cross-sectional view of the granular medicine diffusion chamber 17. These auxiliary air passages 20 are provided to supply outside air into the granular medicine diffusion chamber 17.

On the other hand, a portion denoted by reference sign 21 is the boring tool used to prick holes in the capsule K. The boring tool 21 is mainly constructed by a support portion 22 movably supported within the boring tool guide 3, pins 23, 23 fixedly connected at their base end to the support portion 22 and being insertable at their tip ends into the respective pin insertion holes 11B, 11B, 12A, 12A, and a return spring 24 disposed between the support portion 22 and the holder accommodation portion 5.

The boring tool 21 is used to prick four holes H, H, . . . in the capsule K in such a manner as to penetrate the capsule in the radial direction, by pushing the support portion 22 into the boring tool guide 3 against the bias of the return spring 24, and by inserting the pins 23, 23 into the respective pin insertion holes 11B, 11B, 12A, 12A, and by radially penetrating the capsule K by the tips of the pins 23, 23. When removing the pushing force on the support portion 22, the support portion 22 and the pins 23, 23 return to their initial positions by way of the bias of the return spring 24.

The inhalant medicator of the embodiment is constructed as previously discussed. Hereinbelow described in detail in reference to FIGS. 9 through 11, the preparatory operation of the inhalant medication through which the patient inhales the granular medicines, and the flow of air and granular medicines during inhalation. FIG. 11 shows the diffusion chamber inflow passage 18 and the diffusion chamber outflow passage 19 (both not appearing at the actual cross section), for the purpose of explaining air flow within the granular medicine diffusion chamber 17.

As regards the preparatory operation of inhalant medication, first of all, the capsule holder 6 is pulled out of the holder accommodation portion 5 of the body 2, and then the capsule K is inserted into the capsule holding portion 7. Thereafter, the capsule holder 6 is accommodated in the holder accommodation portion 5 (see FIG. 10).

Next, the support portion 22 of the boring tool 21 is pushed in along the boring tool guide 3, and thus the tips of each of the pins 23 are inserted into the upper pin insertion holes 11B and 12A and then penetrate the capsule K, and further approach to the lower pin insertion holes 11B and 12A. In this manner, as can be seen in FIG. 11, four holes H are formed or pricked in the capsule K.

Under this condition, when the patient draws his or her breath while taking the inhalant port 13 in his or her mouth as seen in FIG. 11, air flows through the inflow air passageways 11, 11 via the holes H to the capsule K, with the result that granular medicines in the capsule K are blended. Air flow containing the granular medicines flow from the capsule K through the holes H, and then flow out within the outflow air passageways 12, 12. The granular medicines, flowing into the granular medicine diffusion chamber 17 together with the air fed from the outflow air passageways 12, can be further diffused by virtue of the air flow occurring in the granular medicine diffusion chamber 17.

As discussed above, in the inhalant medicator of the embodiment, the granular medicine diffusion chamber 17 is equipped at the side of the inhalant port 13 with the granular medicine inflow opening 17A and at the side of the capsule housing hole 9 with the granulate medicine outflow opening 17B. On the other hand, the diffusion chamber block 14 is formed therein with the diffusion chamber inflow passage 18 communicating the outflow air passageway 12 with the granular medicine inflow opening 17A, the diffusion chamber outflow passage 19 communicating the granular medicine outflow opening 17B with the inhalant port 13, and the auxiliary air passage 20 communicating the auxiliary air inflow opening 17C. Therefore, there results in counter-flow vortex flowing from the other axial end to the one axial end of the medicator body within the granular medicine diffusion chamber 17. Thus, the granular medicines, supplied into the granular medicine diffusion chamber 17, are effectively blended by way of the counter-flow vortex. For the reasons set out above, even in case of the use of granular medicines having a strong condensation property (bad dispersion) or a powdered medicine having a greatly increased tendency to be charged with static electricity or the like, it is possible to finely break and micronize or atomize a lump of granular medicines by way of such turbulent air flow, thus effectively diffusing the granular medicines.

Figure 5:
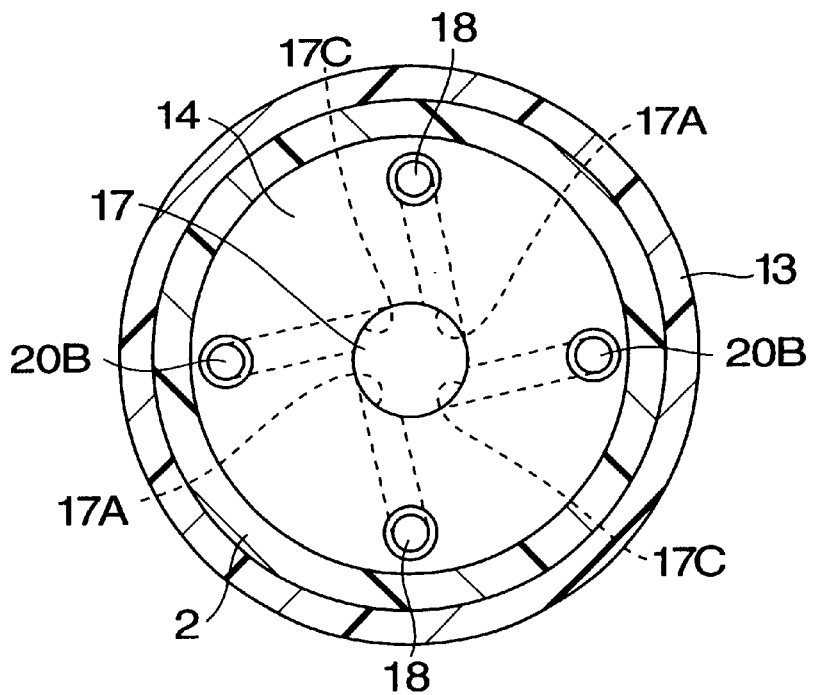
Figure 6:
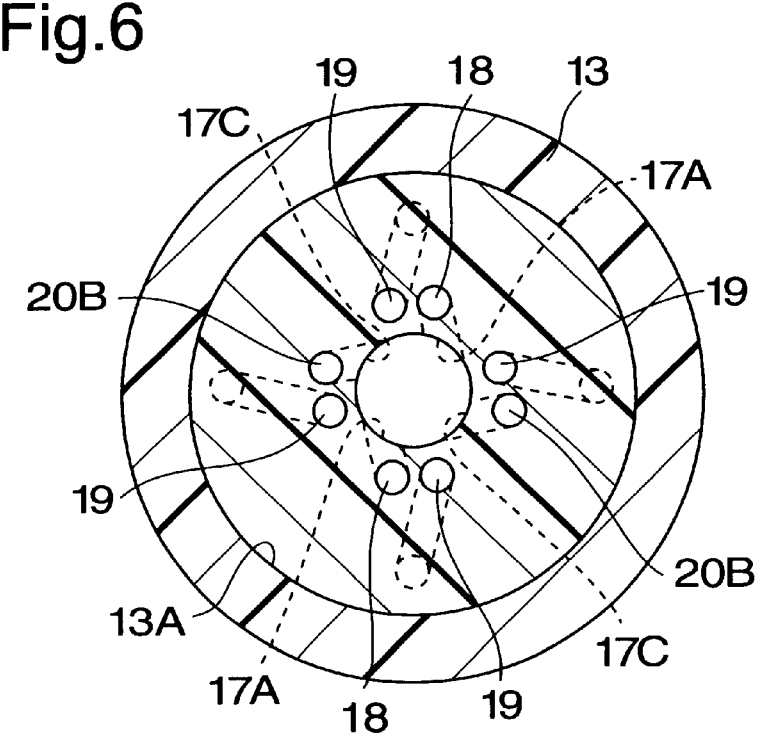
Figure 7:
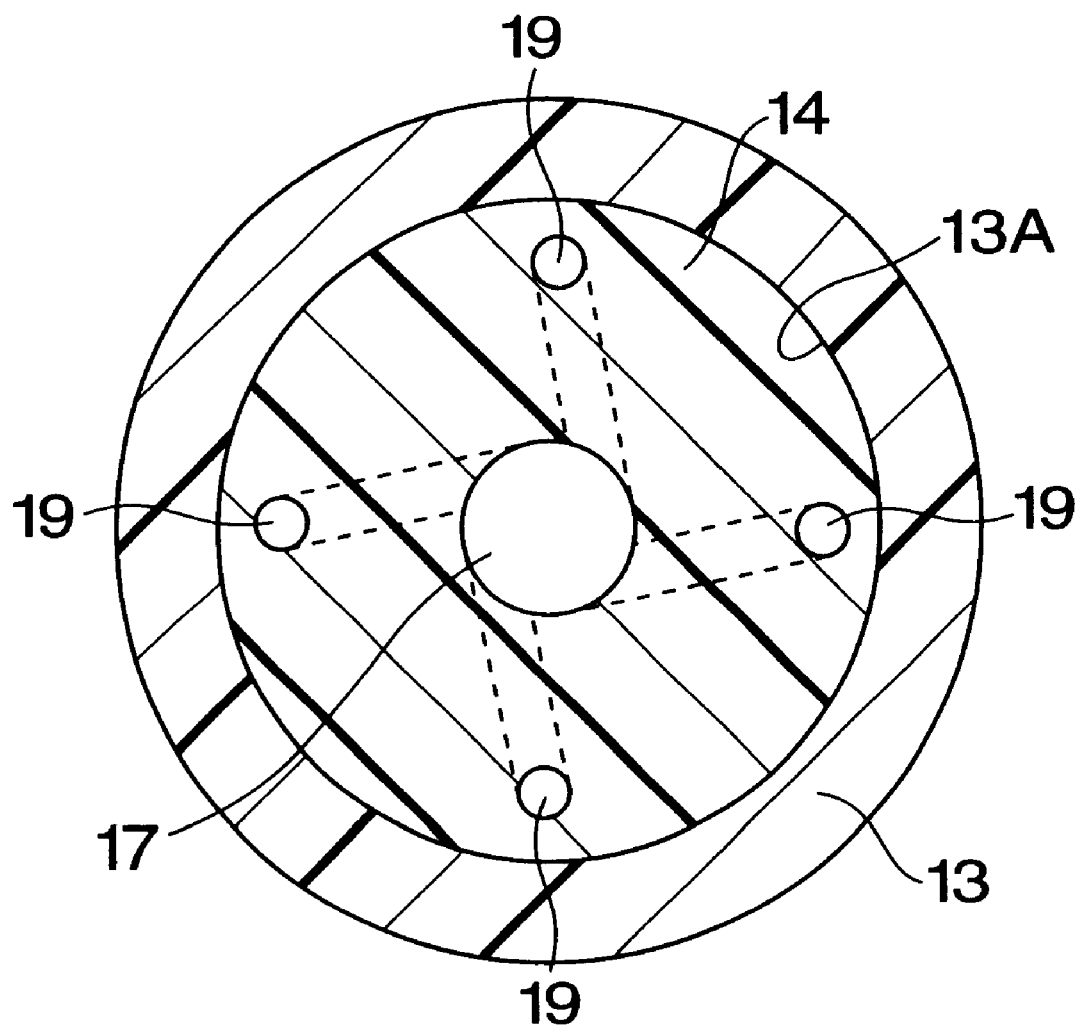
Figure 8:
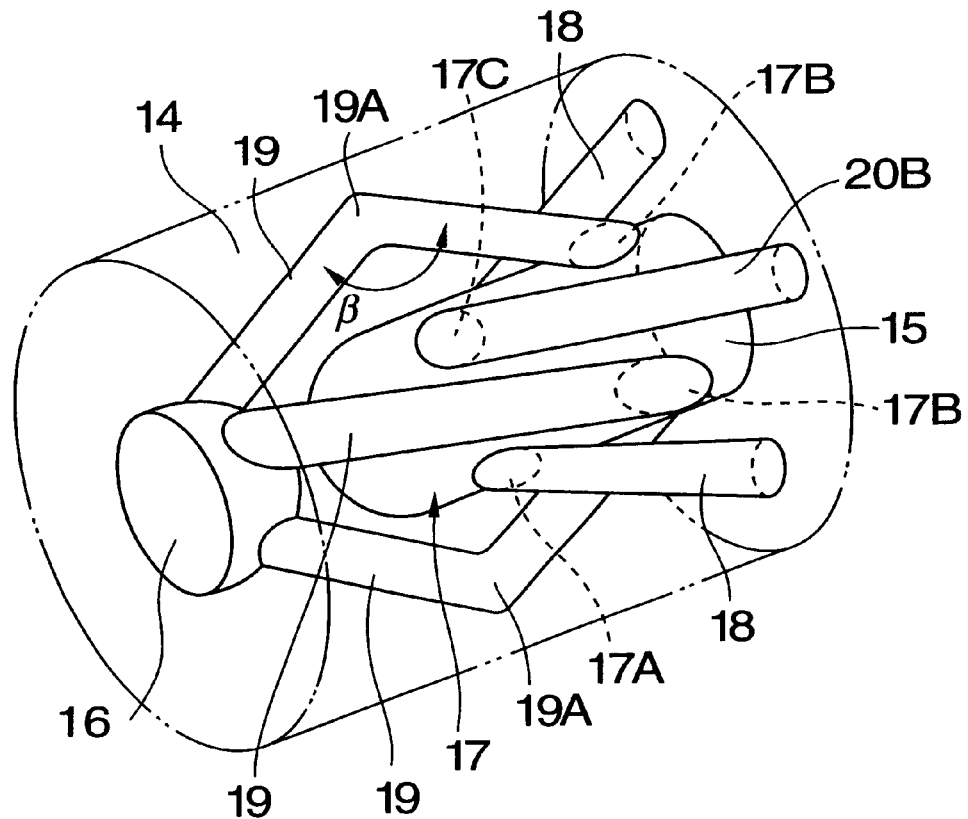
Figure 9:
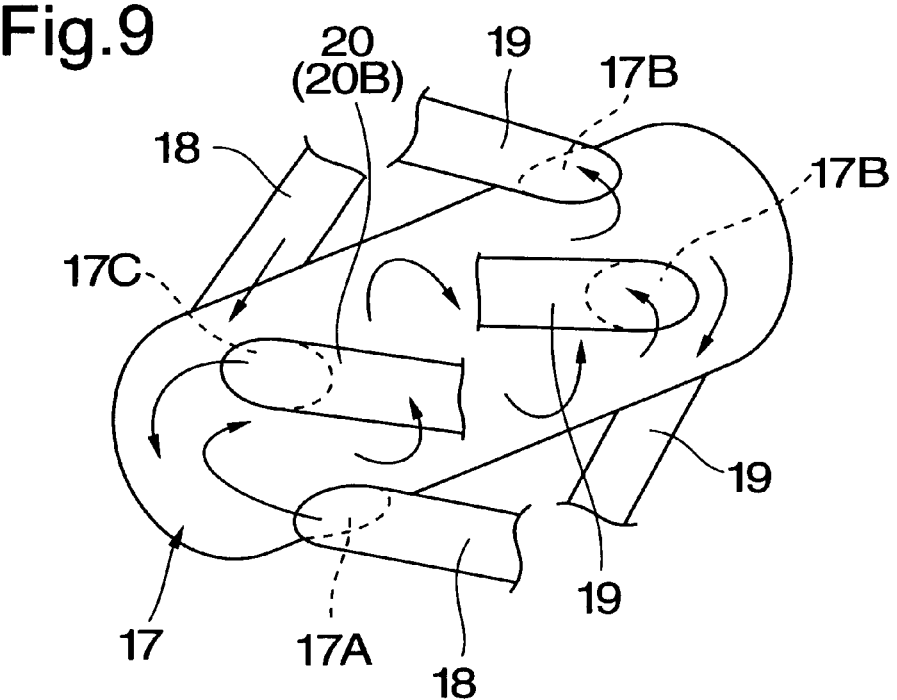
Figure 10:
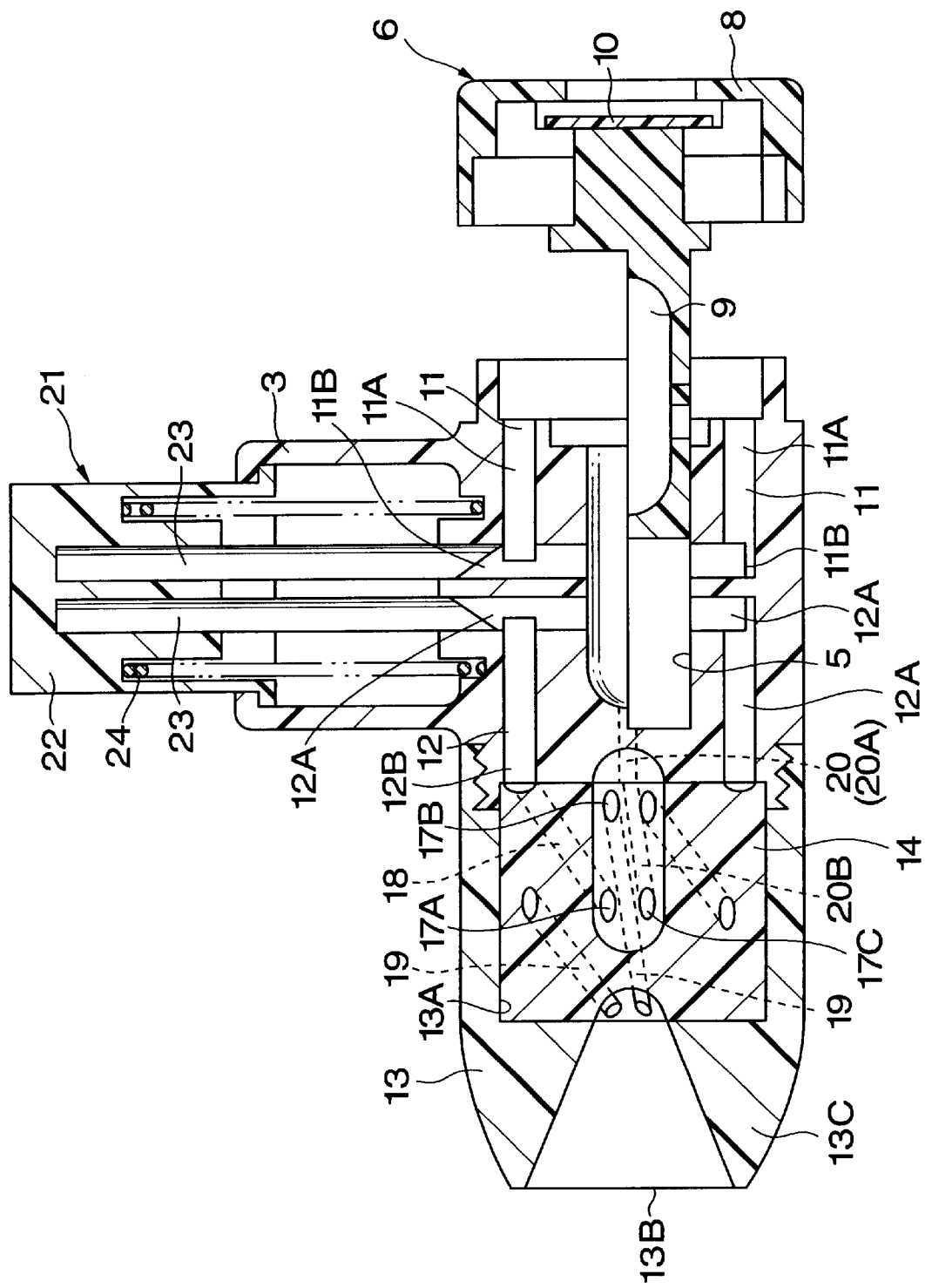

Additionally, as can be seen from FIG. 5, each of the diffusion chamber inflow passages 18 is provided to open to the eccentric position with respect to the longitudinal axis of the granular medicine diffusion chamber 17 so that each of the diffusion chamber inflow passages 1 8 extends in a direction tangent to the granular medicine diffusion chamber 17 as seen from the lateral cross-sectional view of the granular medicine diffusion chamber 17. Thus, it is possible to give a whirling flow action to air flowing from each of the diffusion chamber inflow passages 18 into the granular medicine diffusion chamber 17, thereby ensuring turbulent air flow created by adding the whirling air flow to the counter-flow vortex within the granular medicine diffusion chamber 17. As a result, by virtue of the turbulent air flow, it is possible to promote micronization or atomization of the granular medicines.

Furthermore, the angle α of the connecting portion which connects the diffusion chamber inflow passage 18 and the outflow passage 12B, is an obtuse angle, while the angle β of the bent portion 19A of the diffusion chamber outflow passage 19 is an obtuse angle. Thus, it is possible to prevent the granular medicines fed through the diffusion chamber inflow passage 18 and the diffusion chamber outflow passage 19 from being accumulated in the bent portion, and thereby it is possible to effectively carry the granular medicines.

As described above, according to the inhalant medicator of the embodiment, it is possible to finely break or atomize granular medicines flowing out of the capsule K by way of counter-flow vortex created within the granular medicine diffusion chamber 17, and thus to promote atomization of the granular medicines.

As a result of this, it is possible to prescribe a specified amount of granular or powdered medicines via the oral cavity and trachea of a patient into lungs of the patient during medication, thus enhancing medical benefits of the granular or powdered medicines. This enhances the reliability of the inhalant medicator.

In the shown embodiment, the block mounting hole 13A of the inhalant port 13 and the diffusion chamber block 14 are separated from each other, however the invention is not limited to the particular embodiments shown and described herein. In lieu thereof, the diffusion chamber block 14 may be formed integral with the inhalant port 13.

In the shown embodiment, the capsule holder 6 is detachable with respect to the holder accommodation portion 5 of the body 2, and the capsule k filled with granular medicines is accommodated in the capsule holder 6, however the invention is not limited to the particular embodiments shown and described herein. Alternatively, the capsule holder may be deleted, and the granular medicine accommodation chamber may be directly formed in the medicator body itself. In this case, granular medicines can be charged directly into the granular medicine accommodation chamber.

As explained above, according to the invention recited in claim 1, a granular medicine diffusion chamber is provided in a medicator body and located between a granular medicine accommodation chamber and an inhalant port. The granular medicine diffusion chamber is formed at a side of the inhalant port with an inflow opening and at a side of the granular medicine accommodation chamber with an outflow opening. The granular medicine diffusion chamber is formed therein with a diffusion chamber inflow passage communicating an outflow air passageway with the inflow opening of the granular medicine diffusion chamber, and a diffusion chamber outflow passage communicating the outflow opening with the inhalant port. Therefore, when a patient draws his or her breath while taking the inhalant port in his or her mouse, granular medicines can be carried into the granular medicine diffusion chamber by way of fluid flow of air fed through the granular medicine diffusion chamber. At this time, there occurs counter-flow vortex flowing from the other axial end to one axial end of the medicator body within the granular medicine diffusion chamber. As a result of this, the granular medicines fed into the granular medicine diffusion chamber, are blended by way of the counter-flow vortex. Thus, even in case of the use of massive granular medicines having a bad dispersion property, it is possible to finely break and atomize the granular medicines by virtue of the counter-flow vortex occurring in the granular medicine diffusion chamber. As a result, it is possible to effectively prescribe a specified amount of granular or powdered medicines into lungs of the patient during medication, thus enhancing medical benefits of the granular or powdered medicines. This enhances the reliability of the inhalant medicator.

According to the invention recited in claim 2, the bending angle of a connecting portion which connects the outflow air passageway and the diffusion chamber inflow passage, is an obtuse angle. Thus, it is possible to prevent the granular medicines, fed through the diffusion chamber inflow passage into the granular medicine diffusion chamber, from being accumulated in the connecting portion. As a consequence, it is possible to effectively carry the granular medicines.

According to the invention recited in claim 3 or 4, the diffusion chamber inflow passage is formed with a bent portion striding over the diffusion chamber inflow passage. Thus, it is possible to prevent the granular medicines fed through the diffusion chamber inflow passage and the diffusion chamber outflow passage from being accommodated in the bent portion, thus carrying effectively the granular medicines, and consequently prescribing the granular medicines into lungs of a patient.

According to the invention recited in claim 5, 6 or 7, the diffusion chamber inflow passage is provided to open to the eccentric position with respect to the longitudinal axis of the granular medicine diffusion chamber so that the diffusion chamber inflow passage extends in a direction tangent to the granular medicine diffusion chamber. Thus, it is possible to give a whirling flow action to air flowing from the outflow air passageway into the granular medicine diffusion chamber, thereby ensuring turbulent air flow created by adding the whirling air flow to counter-flow cortex within the granular medicine diffusion chamber. As a consequence, by virtue of the turbulent air flow, it is possible to promote micronization or atomization of the granular medicines.

What is claimed is:

1. An inhalant medicator comprising:

a medicator body formed at one axial end with a granular medicine accommodation chamber and at the other axial end with an inhalant port for inhalation of granular medicines;

an inflow air passageway communicating an atmosphere side with the granular medicine accommodation chamber for supplying air into the granular medicine accommodation chamber of the medicator body;

an outflow air passageway through which the granular medicines of the granular medicine accommodation chamber are flown out;

a granular medicine diffusion chamber disposed between the inhalant port and the granular medicine accommodation chamber and formed with an inflow opening located at a side of the inhalant port and an outflow opening located at a side of the granular medicine accommodation chamber;

a diffusion chamber inflow passage communicating the outflow air passageway with the inflow opening of the granular medicine diffusion chamber; and a diffusion chamber outflow passage communicating the outflow opening of the granular medicine diffusion chamber with the inhalant port.

2. The inhalant medicator as claimed in claim 1, wherein a bending angle of a connecting portion which connects the outflow air passageway and the diffusion chamber inflow passage, is configured to form an obtuse angle.

3. The inhalant medicator as claimed in claim 1, wherein the diffusion chamber outflow passage has a bent portion striding over the diffusion chamber inflow passage.

4. The inhalant medicator as claimed in claim 2, wherein the diffusion chamber inflow passage is provided to open to an eccentric position with respect to a longitudinal axis of the granular medicine diffusion chamber so that the diffusion chamber inflow passage extends in a direction tangent to the granular medicine diffusion chamber as seen from a lateral cross-sectional view of the granular medicine diffusion chamber.

5. The inhalant medicator as claimed in claim 2, wherein the diffusion chamber outflow passage has a bent portion striding over the diffusion chamber inflow passage.

6. The inhalant medicator as claimed in claim 5, wherein the diffusion chamber inflow passage is provided to open to an eccentric position with respect to a longitudinal axis of the granular medicine diffusion chamber so that the diffusion chamber inflow passage extends in a direction tangent to the granular medicine diffusion chamber as seen from a lateral cross-sectional view of the granular medicine diffusion chamber.

7. The inhalant medicator as claimed in claim 1, wherein the diffusion chamber inflow passage is provided to pen to an eccentric position with respect to a longitudinal axis of the granular medicine diffusion chamber so that the diffusion chamber inflow passage extends in a direction tangent to the granular medicine diffusion chamber as seen from a lateral cross-sectional view of the granular medicine diffusion chamber.

* * * * *